United States Patent
Sugawara et al.

(10) Patent No.: US 9,717,987 B2
(45) Date of Patent: Aug. 1, 2017

(54) INDIVIDUAL DISCRIMINATION DEVICE AND INDIVIDUAL DISCRIMINATION METHOD

(75) Inventors: Akihiko Sugawara, Kanagawa (JP); Akio Ohba, Kanagawa (JP); Toshiyuki Hiroi, Saitama (JP)

(73) Assignees: Sony Corporation, Tokyo (JP); Sony Interactive Entertainment Inc., Tokyo (JP)

( * ) Notice: Subject to any disclaimer, the term of this patent is extended or adjusted under 35 U.S.C. 154(b) by 91 days.

(21) Appl. No.: 14/351,274

(22) PCT Filed: Jul. 2, 2012

(86) PCT No.: PCT/JP2012/004267
§ 371 (c)(1),
(2), (4) Date: Apr. 11, 2014

(87) PCT Pub. No.: WO2013/061492
PCT Pub. Date: May 2, 2013

(65) Prior Publication Data
US 2014/0254902 A1   Sep. 11, 2014

(30) Foreign Application Priority Data
Oct. 26, 2011   (JP) .................. 2011-235327

(51) Int. Cl.
*G06T 7/00*   (2017.01)
*A63F 13/213*   (2014.01)
(Continued)

(52) U.S. Cl.
CPC .......... *A63F 13/213* (2014.09); *A61B 5/0077* (2013.01); *A61B 5/117* (2013.01);
(Continued)

(58) Field of Classification Search
None
See application file for complete search history.

(56) References Cited

U.S. PATENT DOCUMENTS 7,689,833 B2   3/2010   Lange
2005/0281439 A1   12/2005   Lange
(Continued)

FOREIGN PATENT DOCUMENTS

CN   201454059 U   5/2010
EP   2438849 A1 *   4/2012   ......... A61B 5/02416
(Continued)

OTHER PUBLICATIONS

Poh, Ming-Zher, Daniel J. McDuff, and Rosalind W. Picard. "Non-contact, automated cardiac pulse measurements using video imaging and blind source separation." Optics express 18.10 (2010): 10762-10774.*
(Continued)

*Primary Examiner* — Vikkram Bali
*Assistant Examiner* — Tracy Mangialaschi
(74) *Attorney, Agent, or Firm* — Matthew B. Dernier, Esq.

(57) ABSTRACT

A frame storage stores an image obtained by imaging a region of at least part of the body of a user. A vital sign signal detector detects a signal sequence of a vital sign that cyclically varies from plural imaged regions of the body of the user by using captured images of a predetermined number of frames stored in the frame storage. A correlation calculator obtains the correlation between the signal sequences of the vital sign detected from the respective imaged regions of the body. An identity determining section determines whether or not the respective imaged regions of the body belong to the same user based on the correlation
(Continued)

between the signal sequences of the vital sign detected from the respective imaged regions of the body.

10 Claims, 5 Drawing Sheets

(51) Int. Cl.
| | |
|---|---|
| *A63F 13/212* | (2014.01) |
| *A61B 5/117* | (2016.01) |
| *A61B 5/00* | (2006.01) |
| *G06K 9/00* | (2006.01) |
| *G06F 3/01* | (2006.01) |
| *G06F 3/03* | (2006.01) |
| *A61B 5/024* | (2006.01) |
| *A61B 5/11* | (2006.01) |
| *A61B 5/113* | (2006.01) |
| *G06K 9/34* | (2006.01) |
| *G06K 9/62* | (2006.01) |

(52) U.S. Cl.
CPC .......... *A61B 5/7246* (2013.01); *A63F 13/212* (2014.09); *G06F 3/011* (2013.01); *G06F 3/017* (2013.01); *G06F 3/0304* (2013.01); *G06K 9/00362* (2013.01); *G06K 9/00496* (2013.01); *G06T 7/0016* (2013.01); *A61B 5/024* (2013.01); *A61B 5/1102* (2013.01); *A61B 5/113* (2013.01); *A63F 2300/1093* (2013.01); *A63F 2300/6045* (2013.01); *A63F 2300/69* (2013.01); *G06F 2203/011* (2013.01); *G06K 9/00771* (2013.01); *G06K 9/342* (2013.01); *G06K 9/6212* (2013.01); *G06K 2009/00939* (2013.01)

(56) References Cited

U.S. PATENT DOCUMENTS

| | | | |
|---|---|---|---|
| 2008/0086533 A1 | 4/2008 | Neuhauser et al. | |
| 2011/0251021 A1* | 10/2011 | Zavadsky ............. | A63B 21/00 482/5 |
| 2011/0311119 A1* | 12/2011 | Jeanne ................. | G06T 7/20 382/128 |
| 2011/0311143 A1* | 12/2011 | Cennini ............ | G06K 9/00255 382/191 |

FOREIGN PATENT DOCUMENTS

| | | | | |
|---|---|---|---|---|
| GB | WO 2011021128 A2 * | 2/2011 | ......... | G06K 9/00496 |
| JP | 2005218507 A | 8/2005 | | |
| JP | 2005534378 A | 11/2005 | | |
| JP | 2008123360 A | 5/2008 | | |
| JP | 2008181220 A | 8/2008 | | |
| JP | 2009544080 A | 12/2009 | | |
| JP | 2011110181 A | 6/2011 | | |
| JP | 2011130996 A | 7/2011 | | |
| WO | 2004012388 A1 | 2/2004 | | |
| WO | 2008008899 A3 | 11/2008 | | |
| WO | 2011021128 A2 | 2/2011 | | |

OTHER PUBLICATIONS

Sun, Yu, et al. "Comparison of scientific CMOS camera and webcam for monitoring cardiac pulse after exercise." SPIE Optical Engineering+ Applications. International Society for Optics and Photonics, Sep. 2011.*

Verkruijsse, W., and M. P. Bodlaender. A novel biometric signature: multi-site, remote (> 100 m) photo-plethysmography using ambient light. Philips Research, 2010.*

European Search Report for corresponding EP Patent Application 12843864.5-1660, dated May 8, 2015.

International Preliminary Report on Patentability and Written Opinion for corresponding PCT/JP2012/004267, dated May 8, 2014.

International Search Report for corresponding PCT/JP2012/004267, dated Oct. 2, 2012.

Office Action for corresponding JP Patent Application 2011-235327, dated Aug. 4, 2015.

Office Action for corresponding CN Application No. 2012800513938, 5 pages, dated Mar. 3, 2016.

Office Action for corresponding JP Application No. 2015198474, 11pages, dated Oct. 18, 2016.

* cited by examiner

INDIVIDUAL DISCRIMINATION DEVICE AND INDIVIDUAL DISCRIMINATION METHOD

TECHNICAL FIELD

This invention relates to device and method to carry out individual discrimination from a captured image.

BACKGROUND ART

Among home-use game machines are ones equipped with a camera. Such a game machine can image a user playing a game to display the image of the user on a game screen and can detect the action of the user from the captured image of the user to reflect it in the game. Furthermore, this game machine can also detect the facial expression of the user from an image of the user photographed by the camera and grasp the mental status of the user in the game playing to reflect it in the progression of the game. In addition, it is also possible that plural players each have a controller to operate the game machine, and a game is frequently played by plural persons including family, friends, etc.

Furthermore, in order to detect the degree of nervousness of a user in game playing, the following method is also carried out. Specifically, a sensor to detect the pulse is mounted on the user and the measurement result of the pulse output by the sensor is input to the game machine and reflected in the game.

In Patent Literature 1, a method is described in which a vital sign is measured from temporal change in the density of a captured image of a subject.

CITATION LIST

Patent Literature

[PTL 1]
JP 2005-218507A

SUMMARY

Technical Problem

When plural players each have a controller to operate the game machine or when family and friends are present around in addition to a player having a controller, plural users are included in an image photographed by the camera and therefore individual discrimination needs to be carried out in the captured image. It is also possible to carry out the individual discrimination by recognizing a region of face, hand, etc. from the image. However, if a hand of a player operating the controller intersects a hand of another person in game playing, it is often difficult to associate the hand with the face.

The present invention is made in view of such a problem and an object thereof is to provide individual discrimination device and individual discrimination method that are capable of accurately carrying out individual discrimination in a captured image.

Solution to Problem

To solve the above-described problem, an individual discrimination device of a certain aspect of the present invention includes a storage that stores an image obtained by imaging a region of at least part of a body of a user and a vital sign signal detector that detects a signal sequence of a vital sign that cyclically varies from a plurality of imaged regions of the body of the user by using captured images of a predetermined number of frames stored in the storage. The individual discrimination device further includes a correlation calculator that obtains the correlation between the signal sequences of the vital sign detected from the imaged regions of the body and an identity determining section that determines whether or not the imaged regions of the body belong to the same user based on the correlation between the signal sequences of the vital sign detected from the imaged regions of the body.

Another aspect of the present invention is an individual discrimination method. This method includes a vital sign signal detection step of detecting a signal sequence of a vital sign that cyclically varies from a plurality of imaged regions of a body of a user by using and referring to captured images of a predetermined number of frames from a memory that stores an image obtained by imaging a region of at least part of the body of the user. The method further includes a correlation calculation step of obtaining the correlation between the signal sequences of the vital sign detected from the imaged regions of the body and an identity determination step of determining whether or not the imaged regions of the body belong to the same user based on the correlation between the signal sequences of the vital sign detected from the imaged regions of the body.

What are obtained by translating arbitrary combinations of the above constituent elements and expressions of the present invention among method, device, system, computer program, data structure, recording medium, and so forth are also effective as aspects of the present invention.

Advantageous Effect of Invention

According to the present invention, individual discrimination can be accurately carried out from a captured image.

DESCRIPTION OF EMBODIMENTS

Figure 1:
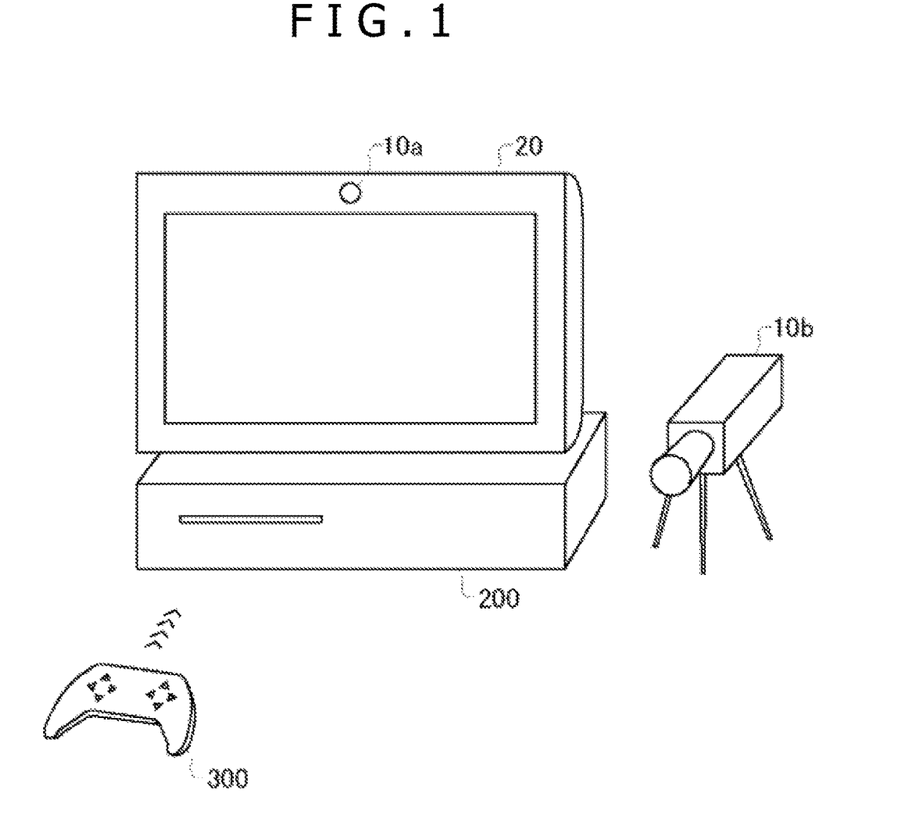
FIG. 1 is a configuration diagram of a game system according to an embodiment.

FIG. 1 is a configuration diagram of a game system according to an embodiment. The game system includes a game machine 200, a display 20, a controller 300, and cameras 10a and 10b.

The controller 300 is connected to the game machine 200 in a wireless or wired manner. The camera 10a is incorporated in the display 20 as a built-in component and photographs a user having the controller 300 and playing a game and friend, family, etc. who are together with the user. A screen of the game is displayed on the display 20. The video camera 10b can perform photographing with focus on part of the body of the user, specifically e.g. the hand holding the controller, the face of a specific user, or the like, and the photographed image is input to the game machine 200. The display 20 can also display an image of a user photographed by the cameras 10a and 10b.

Although the embodiment will be explained by taking game playing as an example here, the embodiment is not limited to the game and can be applied also to the case of watching video or the like by a television screen.

Figure 2:
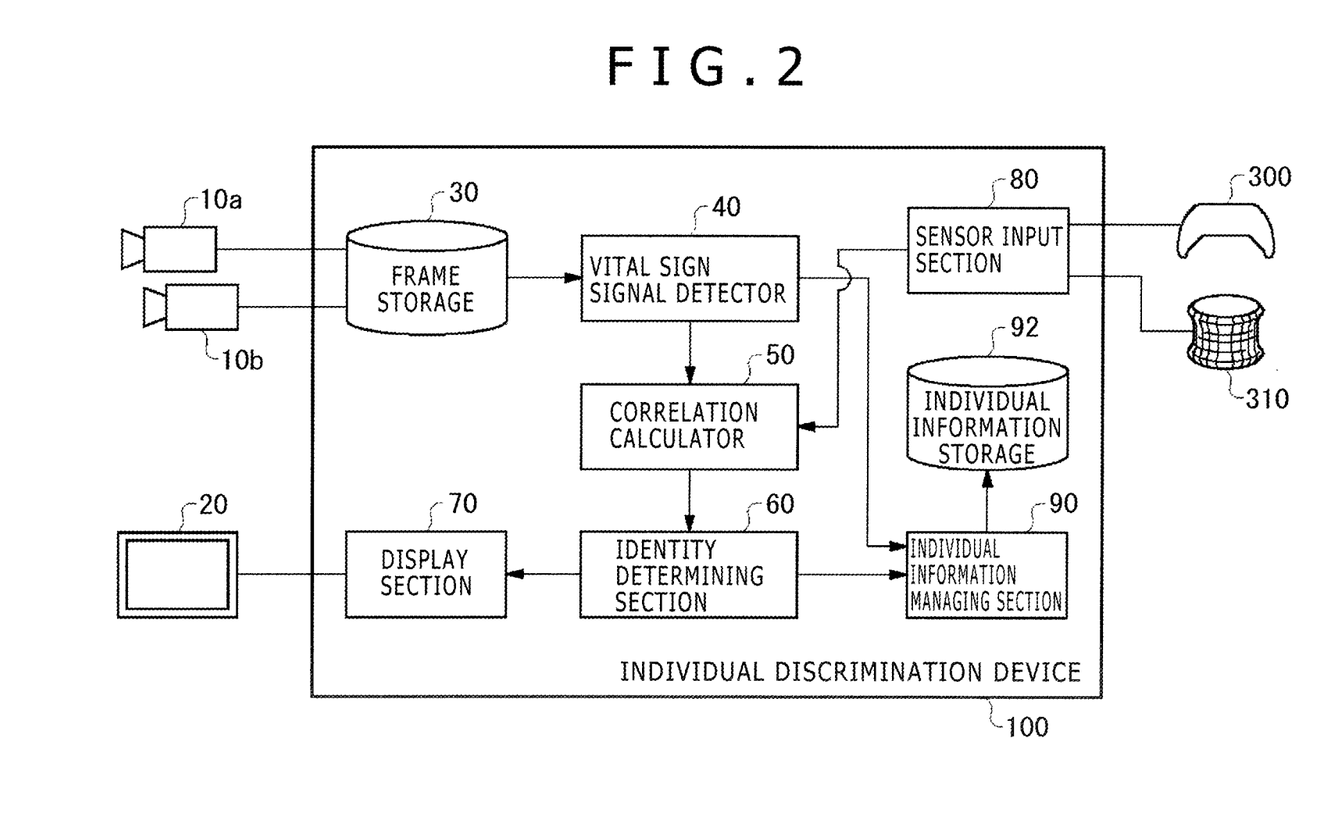
FIG. 2 is a configuration diagram of an individual discrimination device according to the embodiment.

FIG. 2 is a configuration diagram of an individual discrimination device 100 according to the embodiment. To the individual discrimination device 100, the plural cameras 10a and 10b, the display 20, the controller 300, and a wearable sensor 310 are connected. The individual discrimination device 100 is a functional configuration mounted in the game machine 200 in FIG. 1.

The cameras 10a and 10b photograph a partial or whole region of the body of a user. Either only one camera or plural cameras may be used. For example, plural persons including a player of a game may be photographed by one camera. Alternatively, a camera to photograph the player mainly and a different camera to photograph the whole of plural persons including or not including the player may be provided. Alternatively, a certain camera may photograph a hand of a user and a different camera may photograph the face of the user. The photographed image is stored in a frame storage 30.

A vital sign signal detector 40 detects a signal sequence of a vital sign that cyclically varies from an imaged region of the body of a user by using photographed images of a predetermined number of frames stored in the frame storage 30. The vital sign signal detector 40 can detect the signal sequence of the vital sign that cyclically varies by sensing change in the vibration or light absorption characteristics of the skin in the body imaged region in the photographed images of the predetermined number of frames. The vital sign that cyclically varies is a vital sign such as the heartbeat or breathing. A waveform data sequence of a vital sign such as the heartbeat can be acquired if change in the vibration or light absorption characteristics of the skin in a body part where the skin is exposed in photographed images of a frame number such as five frames or so is detected. The change in the light absorption characteristics is detected as change in the density and color of the image of the skin.

The vital sign signal detector 40 may divide the imaged region into small regions and detect a signal sequence of a vital sign for each of the divided small regions. To suppress the calculation amount and suppress noise, it is more preferable to detect a signal sequence of a vital sign for each of regions with a predetermined area.

The method for measuring the pulse by detecting change in the vibration or light absorption characteristics of the skin in a body imaged region is described in detail in the following documents for example.

"Heart rate measurement based on a time-lapse image," Medical Engineering and Physics, 2007

"Advancements in non-contact, multiparameter physiological measurements using a webcam," IEEE Trans Biomed Eng, 2010.

"Non-contact, automated cardiac pulse measurements using video imaging and blind source separation," Optics Express, 2010.

A correlation calculator 50 obtains the correlation between signal sequences of a vital sign detected from the respective imaged regions of the body. When a signal sequence of a vital sign detected in a first body imaged region is defined as H1($t$) and a signal sequence of the vital sign detected in a second body imaged region is defined as H2($t$), a correlation R between the two signal sequences H1($t$) and H2($t$) can be obtained by the following expression. However, it is also possible to use a calculation expression different from it.

$$R = \frac{\sum_t \{H_1(t) * H_2(t)\}}{\sqrt{\sum_t \{H_1(t)\}^2} * \sqrt{\sum_t \{H_2(t)\}^2}} \quad \text{[Expression 1]}$$

An identity determining section 60 determines whether or not the respective imaged regions of the body belong to the same user based on the correlation between the signal sequences of the vital sign detected from the respective imaged regions of the body. If the correlation R between the signal sequence H1($t$) of the vital sign of the first body imaged region and the signal sequence H2($t$) of the vital sign of the second body imaged region is higher than a predetermined threshold T, the identity determining section 60 determines that the first body imaged region and the second body imaged region belong to the same person. If the correlation R between the two signal sequences H1($t$) and H2($t$) is equal to or lower than the predetermined threshold T, the identity determining section 60 determines that the first body imaged region and the second body imaged region belong to different persons.

The first body imaged region and the second body imaged region may be ones imaged by the different cameras 10a and 10b. For example, if a hand of the user is imaged by the first camera 10a and a face of the user is imaged by the second camera 10b, the correlation R is calculated between the signal sequence H1($t$) of the vital sign detected from the captured image of the hand of the user and the signal sequence H2($t$) of the vital sign detected from the captured image of the face of the user. Then, the identity determining section 60 determines that the imaged hand and face of the user belong to the same person if the correlation R is high, and determines that the imaged hand and face of the user belong to different persons if the correlation R is low. In this manner, even if hand and face of the user are not necessarily ones imaged by the same camera, individual discrimination can be carried out by obtaining the correlation between signal sequences of a vital sign detected from the hand and the face.

A display section 70 carries out the same highlighting for plural imaged regions of the body determined to belong to the same person and displays the imaged regions on the display 20. For example, the display section 70 displays plural imaged regions of the body determined to belong to the same person with the same color. This allows the user to check, in the screen, how the individual discrimination device 100 has carried out individual discrimination.

A sensor input section 80 receives input of a signal sequence of a vital sign that cyclically varies from a sensor mounted in the controller 300 or the wearable sensor 310. For example, the controller 300 is equipped with a pulse sensor and so forth and the pulse of an operator of the controller 300 can be measured and input to the sensor input section 80. Furthermore, it is also possible that a user wears the wearable sensor 310 such as a pulse sensor on a wrist, ankle, etc. and the pulse is measured and input to the sensor input section 80.

The correlation calculator 50 may obtain the correlation between a signal sequence of a vital sign obtained from the sensor input section 80 and a signal sequence of the vital sign detected from a body imaged region. Based on the correlation between the signal sequence of the vital sign obtained from a sensor and the signal sequence of the vital sign detected from the body imaged region, the identity determining section 60 can determine whether or not this body imaged region belongs to the operator of the controller or the sensor wearer. For example, if the correlation between a signal sequence of a vital sign detected from an imaged region of a hand of a user making a specific gesture and a signal sequence of the vital sign obtained from a sensor is high, the identity determining section 60 can determine that the hand making the gesture belongs to the operator of the controller. This allows grasping that the gesture by the hand and the operation by the controller are made by the same person and makes it possible to treat both the gesture by the hand and the operation by the controller as input from the same user to the game.

An individual information managing section 90 stores body imaged regions determined to belong to the same person by the identity determining section 60 in an individual information storage 92 as individual information of a user and manages the individual information. Furthermore, the individual information managing section 90 associates a flag indicating the operator of the controller or the sensor wearer with a specific body imaged region determined to belong to the operator of the controller or the sensor wearer and manages the imaged region. This can identify the body region of the operator of the controller or the sensor wearer from plural users included in a captured image and determine the degree of satisfaction of the user in game playing from the facial expression of the operator of the controller for example.

The vital sign signal detector 40 obtains a feature indicating the periodicity of a vital sign of an individual by performing a discrete Fourier transform of a signal sequence of the vital sign to detect the frequency. Alternatively, it obtains the feature indicating the periodicity of the vital sign of the individual by obtaining the autocorrelation of a signal sequence of the vital sign to detect the cycle of the signal. For example, if the vital sign is the heartbeat, the heart rate is obtained as the feature indicating the periodicity of the vital sign of an individual. The individual information managing section 90 classifies the feature indicating the periodicity of the vital sign of an individual on each user basis and stores it in the individual information storage 92 as individual information. This can detect the degree of excitement of a user in game playing and so forth, such as increase in the heart rate of a specific user, for example.

The convenience and entertainment can be enhanced by feeding back the degree of satisfaction and the degree of excitement of the user obtained in this manner to the game progression. For example, if it is determined that the user is relaxed based on the degree of excitement of the user, short-term control to give a sudden change to the game progression may be carried out. Alternatively, the level of proficiency of the user in operation of the controller, the rule of the game, and so forth may be grasped based on the degree of satisfaction of the user and long-term control to adjust the speed of the game progression and so forth according to the level of proficiency of the user may be carried out. Furthermore, if the heart rate of the player is too high or return of the heart rate to normal is slow, a proposal to take a rest may be given to the player. Moreover, the degree of satisfaction and the degree of excitement of the user may be recorded and fed back to the game developer via a network or the like to be utilized for update of the game and future game development.

Furthermore, the face of a user different from the player having the controller may be detected by using a face detection function and correlation values of heart rate variation and breathing timing between the user and the player may be regarded as an index indicating empathy with the player to evaluate the degree of enjoyment at the place where the game is played, including observers. For example, in a party game or the like, if the index indicating empathy is low and the place where the game is played lacks in enjoyment although only the player is excited, the game progression can be adjusted based on such an index.

Moreover, the posture of the player may be guessed based on body information of the same individual about face, hand, foot, etc. and advice to correct the posture may be given if an unfavorable posture continues for a long time. In the case of an application with which the body of the player is moved like in yoga, the body information can be used as a factor to determine whether or not the posture of the user is good.

Figure 3A:
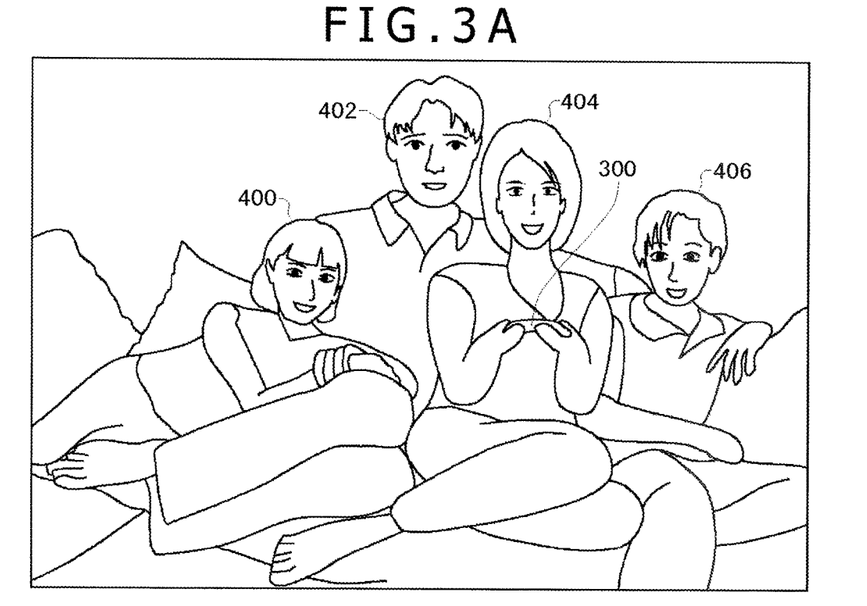
FIG. 3A is a diagram for explaining an image of users photographed by a camera.

FIG. 3A is a diagram for explaining an image of users photographed by the cameras 10a and 10b. Suppose that four users 400, 402, 404, and 406 are watching a game screen in front of the game machine 200. These users are a family and the second right user 404 (mother) holds the controller 300 with the hands. The second left user 402 (father) wears the wearable sensor 310 on a wrist although not shown in the diagram.

Figure 3B:
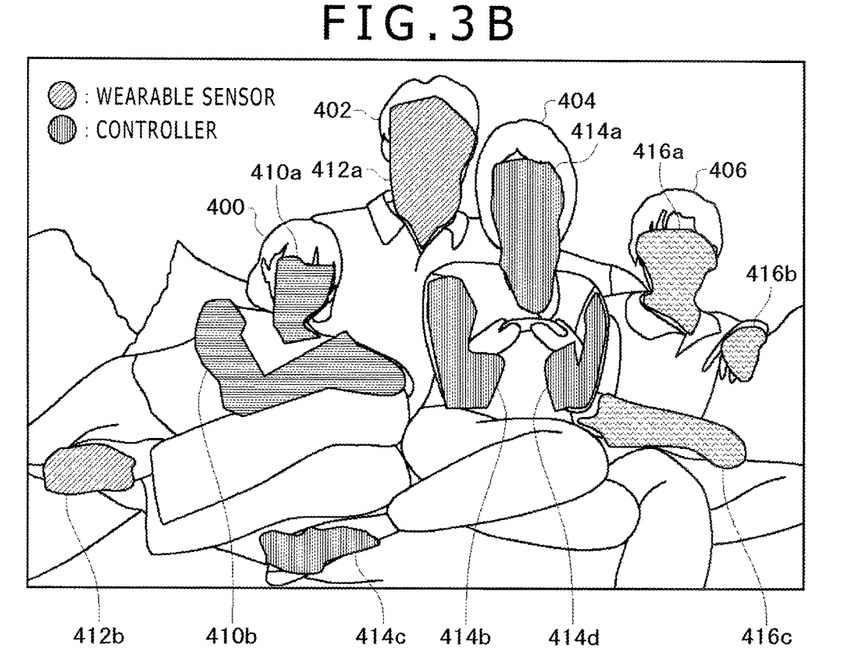
FIG. 3B is a diagram for explaining a determination result of imaged regions of the body by an identity determining section in FIG. 2.

FIG. 3B is a diagram for explaining a determination result of body imaged regions by the identity determining section 60. Two body imaged regions 410a and 410b are determined to belong to the same person 400 because the correlation between signal sequences of a vital sign detected from these imaged regions is higher than a predetermined threshold. The threshold of the correlation used for the identity determination can be experimentally defined to make the accuracy of the identity determination fall within a certain error range.

Similarly, two body imaged regions 412a and 412b are determined to belong to the same person 402 because the correlation between signal sequences of a vital sign is higher than the predetermined threshold. Four body imaged regions 414a, 414b, 414c, and 414d are determined to belong to the same person 404 because the correlation among signal sequences of a vital sign is higher than the predetermined threshold. Three body imaged regions 416a, 416b, and 416c are determined to belong to the same person 406 because the correlation among signal sequences of a vital sign is higher than the predetermined threshold.

Here, because the user 402 (father) wears the wearable sensor 310, a signal sequence of a vital sign of the father can be acquired from the wearable sensor 310. The correlation between the signal sequence of the vital sign from the wearable sensor 310 and the signal sequences of the vital sign of the two body imaged regions 412a and 412b is higher than the predetermined threshold. Thus, the identity determining section 60 determines that these body imaged regions 412a and 412b belong to the wearer of the wearable sensor 310 (here, father). The individual information managing section 90 associates the body imaged regions 412a and 412b with identification information of the wearer of the wearable sensor 310 and stores them in the individual information storage 92.

Furthermore, the user 404 (mother) holds the controller 300 with the hands and a signal sequence of a vital sign of the mother can be acquired from the sensor mounted in the controller 300. The correlation between the signal sequence of the vital sign from the sensor of the controller 300 and the signal sequences of the vital sign of the four body imaged regions 414a, 414b, 414c, and 414d is higher than the predetermined threshold. Thus, the identity determining section 60 determines that these body imaged regions 414a, 414b, 414c, and 414d belong to the operator of the controller 300 (here, mother). The individual information managing section 90 associates the body imaged regions 414a, 414b, 414c, and 414d with identification information of the wearer of the controller 300 and stores them in the individual information storage 92.

Figure 4:
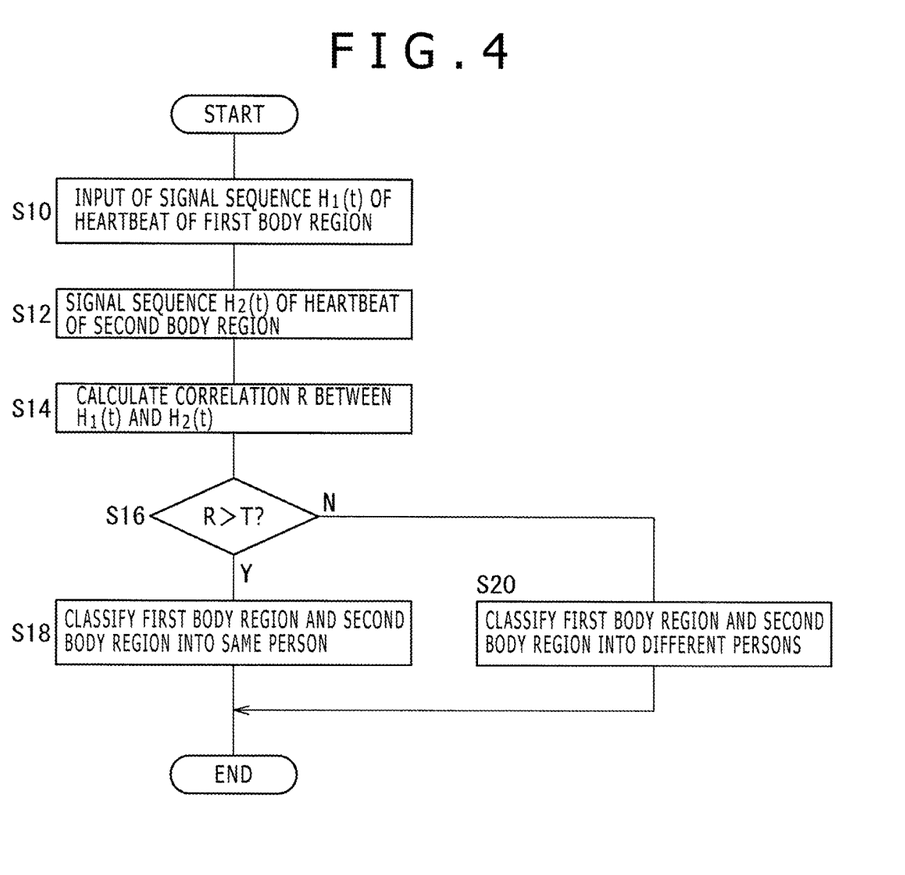
FIG. 4 is a flowchart for explaining an individual discrimination procedure by the individual discrimination device of FIG. 2.

FIG. 4 is a flowchart for explaining an individual discrimination procedure by the individual discrimination device 100. Here, the explanation will be made based on the assumption that the vital sign is the heartbeat.

The vital sign signal detector 40 detects the signal sequence H1(t) of the heartbeat from a first body imaged region (S10). The vital sign signal detector 40 detects the signal sequence H2(t) of the heartbeat from a second body imaged region (S12).

The correlation calculator 50 calculates the correlation R between the first heartbeat signal sequence H1(t) and the second heartbeat signal sequence H2(t) (S14).

If the correlation R is higher than the threshold T (Y of S16), the identity determining section 60 determines that the first body imaged region and the second body imaged region belong to the same person, and the individual information managing section 90 classifies the first body imaged region and the second body imaged region as individual information of this person and registers them in the individual information storage 92 (S18). Thereby, for example hand and face of a certain user are associated as parts belonging to the same person.

If the correlation R is equal to or lower than the threshold T (N of S16), the identity determining section 60 determines that the first body imaged region and the second body imaged region belong to different persons, and the individual information managing section 90 classifies the first body imaged region and the second body imaged region as individual information of the different persons and registers them in the individual information storage 92 (S20). This allows individual discrimination and classification of plural users.

Figure 5:
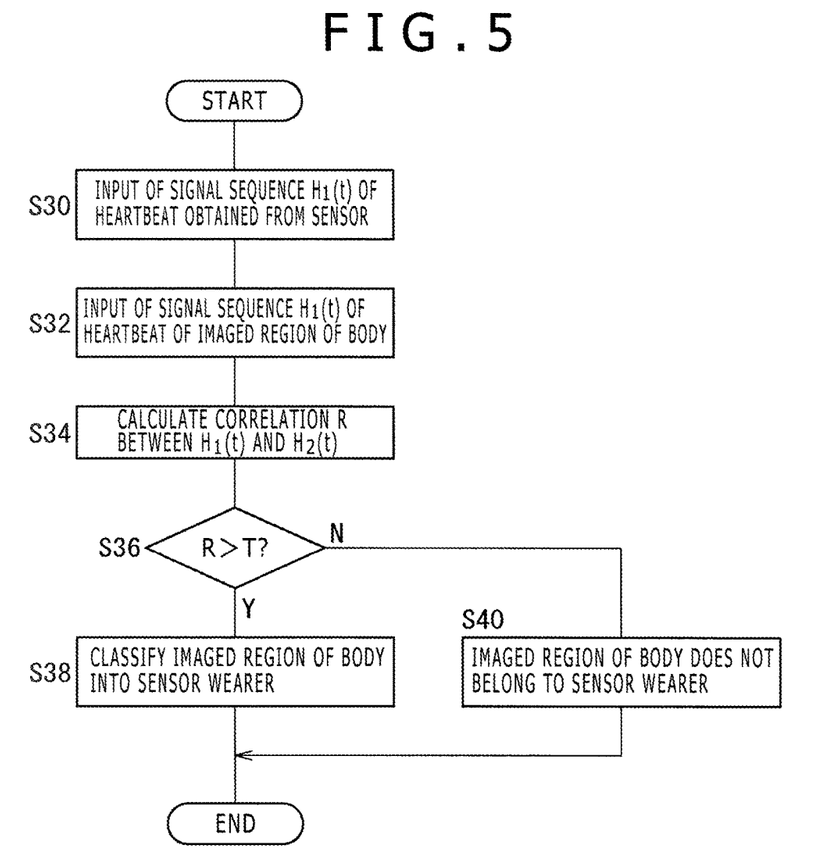
FIG. 5 is a flowchart for explaining another individual discrimination procedure by the individual discrimination device of FIG. 2.

FIG. 5 is a flowchart for explaining another individual discrimination procedure by the individual discrimination device 100.

The sensor input section 80 detects the signal sequence H1(t) of the heartbeat from the sensor mounted in the controller 300 or the wearable sensor 310 worn on the body of a user (S30). The vital sign signal detector 40 detects the signal sequence H2(t) of the heartbeat from a body imaged region obtained by imaging by the cameras 10a and 10b (S32).

The correlation calculator 50 calculates the correlation R between the first heartbeat signal sequence H1(t) and the second heartbeat signal sequence H2(t) (S34).

If the correlation R is higher than the threshold T (Y of S36), the identity determining section 60 determines that the relevant body imaged region belongs to the controller operator or the sensor wearer, and the individual information managing section 90 classifies this body imaged region as individual information of the controller operator or the sensor wearer and registers it in the individual information storage 92 (S38). This allows identification of a body region of the controller operator or the sensor wearer, specifically e.g. the face, and enables control such as changing the progression of the game based on the facial expression of the controller operator or the sensor wearer.

If the correlation R is equal to or lower than the threshold T (N of S36), the identity determining section 60 determines that the relevant body imaged region does not belong to the controller operator or the sensor wearer (S40). This allows differentiation between the controller operator or the sensor wearer and the other users.

In the above description, the method in which identity determination of body imaged regions is carried out based on a vital sign is explained. However, once identity determination of body imaged regions ends, the identity determination of the body imaged regions may be continued without detecting the vital sign by tracking the body imaged regions such as hand and face with use of a technique such as template matching. For example when the user moves the body to a large extent or when the positions of users are exchanged, the identity determination based on the vital sign may be resumed because the tracking will fail.

Although the heartbeat is taken as an example of the vital sign in the embodiment, the breathing may be detected as the vital sign from the vibration of the body of an imaged user. Furthermore, the human has a characteristic that the heart rate increases in inspiratory action and the heart rate decreases in expiratory action. Therefore, the breathing can be detected also from a signal sequence of the heartbeat. A method for detecting the cycle or frequency of the breathing from the heartbeat will be described below.

(1) First, the heart rate is obtained by detecting the frequency from a waveform data sequence of the heartbeat by a Fourier transform. The heart rate may be obtained from the cycle derived by using the autocorrelation of a waveform data sequence of the heartbeat.

(2) Next, the obtained heart rate is consecutively obtained at a time interval equal to or shorter than the heartbeat cycle, specifically e.g. at an interval of 0.5 seconds, to derive a heart rate sequence.

When motion affecting the heart rate is not being performed, heart rate variation corresponding to breathing action appears in the heart rate sequence. The heart rate increases in inspiratory action and the heart rate decreases in expiratory action. Therefore, if the frequency or cycle of the heart rate variation is obtained from the heart rate sequence by a method similar to the above-described (1), it can be regarded as the frequency or cycle of the breathing. The breathing is advantageous in that it can be detected even when clothing is worn. Furthermore, it is also possible to detect whether plural players are in harmony with each other in game playing from the degree of synchronization of the waveforms of the breathing of the players.

As described above, according to the individual discrimination device 100 of the present embodiment, by taking the correlation of temporal change between regions from which the pulse is sensed, regions of the same pulse source can be identified and individual discrimination and classification can be carried out. Even when plural users are included in a captured image, individual discrimination of regions such as face, hand, and foot can be carried out and whether or not the regions belong to the same person can be determined. Furthermore, an image of an imaged hand or face can be associated with a controller operator or sensor wearer based on the correlation with pulse information from a contact sensor of a controller, wearable tool, or the like.

The face, hand, and foot exist at distal places in the body and are also distant from the heart. However, the waveform and frequency of the pulse are substantially the same at the respective parts of the body. An offset depending on the distance from the heart is generated in a waveform data sequence of the pulse of each body part. Due to this, difference is often generated in the phase although the waveform is similar. To respond to such a case, in taking the correlation between waveform data sequences of the pulse of the respective body parts, plural correlations taken with phase offset are obtained and the maximum correlation value among them is employed. This makes it possible to determine whether the pulse waveform data are obtained from the body of the same person even when the body parts are different. A high correlation with pulse waveform data of another person is often instantaneously obtained. However, if the pulse waveform data is observed for a long time, the waveforms become out of synchronization and the phase offset greatly varies with time and thus the high correlation comes not to be obtained.

The present invention is described above based on the embodiment. It will be understood by those skilled in the art that the embodiment is exemplification and various modification examples are possible in combinations of the respective constituent elements and the respective processing processes thereof and such modification examples are also within the scope of the present invention. Such modification examples will be described.

REFERENCE SIGNS LIST

Camera, 20 Display, 30 Frame storage, 40 Vital sign signal detector, 50 Correlation calculator, 60 Identity determining section, 70 Display section, 80 Sensor input section, 90 Individual information managing section, 92 Individual information storage, 100 Individual discrimination device, 200 Game machine, 300 Controller, 310 Wearable sensor.

INDUSTRIAL APPLICABILITY

The present invention can be utilized for a technique to carry out individual discrimination from a captured image.

The invention claimed is:

1. An individual discrimination device comprising:
   a storage that stores an image obtained by imaging a region of at least part of a body of a user playing a video game;
   a vital sign signal detector that detects a signal sequence, of a detected vital sign that cyclically varies, from a plurality of imaged regions of the body of the user by using captured images of a predetermined number of frames stored in the storage;
   a sensor input section that receives input of a signal sequence of a sensed vital sign that cyclically varies from at least one of a sensor mounted in a controller operated by the user and a wearable sensor worn by the user;
   a correlation calculator that obtains a correlation between the signal sequences of the detected vital sign detected from the imaged regions of the body and obtains a correlation between the signal sequence of the sensed vital sign obtained by the sensor input section and at least one of the signal sequences of the detected vital sign detected from the imaged regions of the body;
   an identity determining section that determines, based on the correlation between the signal sequences of the detected vital sign detected from the imaged regions of the body, that the imaged regions of the body belong to a same user and that determines, based on the correlation between the signal sequence of the sensed vital sign obtained by the sensor input section and at least one of the signal sequences of the detected vital sign detected from the imaged regions of the body, that the imaged regions of the body belong to at least one of the operator of the controller and the wearer of the sensor; and
   an individual information management section that feeds back to a progression of the game at least one characteristic of the user, the characteristic being based on the detected signal sequence.

2. The individual discrimination device according to claim 1, wherein the vital sign signal detector detects the signal sequence of the vital sign that cyclically varies by sensing change in vibration or a light absorption characteristic of skin in the imaged region of the body in the captured images of the predetermined number of frames.

3. The individual discrimination device according to claim 1, wherein:
   the vital sign is a heartbeat, and
   the identity determining section determines that the imaged regions of the body belong to the same user based on a correlation between detected signal sequences of the heartbeat.

4. The individual discrimination device according to claim 1, further comprising: a display section that carries out a same highlighting for a plurality of imaged regions of a body determined to belong to the same user.

5. The individual discrimination device according to claim 1, wherein:
   the vital sign signal detector detects the signal sequence of the vital sign that cyclically varies from each of a first body imaged region imaged by a first imager and a second body imaged region imaged by a second imager,
   the correlation calculator obtains a correlation between the signal sequences of the vital sign detected from the first body imaged region and the second body imaged region, and
   the identity determining section determines that the first body imaged region and the second body imaged region belong to the same user based on the correlation between the signal sequences of the vital sign detected from the first body imaged region and the second body imaged region.

6. The individual discrimination device of claim 1, wherein:
   the storage stores a plurality of images, each image being obtained by imaging one or more user body regions;
   the vital sign detector divides each imaged region into a plurality of small regions, each of the small regions presenting a respective signal sequence, of a vital sign that cyclically varies, and detects the respective signal sequences of each of the small regions;
   the correlation obtained by the correlation calculator is a correlation between the signal sequences detected from the small regions; and
   the identity determining section determines that certain imaged regions belong to the same user based on the correlation.

7. An individual discrimination method comprising:
   a vital sign signal detection step of detecting a signal sequence of a detected vital sign that cyclically varies from a plurality of imaged regions of a body of a user playing a video game by using and referring to captured images of a predetermined number of frames from a memory that stores an image obtained by imaging a region of at least part of the body of the user;

a sensor input step of receiving input of a signal sequence of a sensed vital sign that cyclically varies from at least one of a sensor mounted in a controller operated by the user and a wearable sensor worn by the user;

a correlation calculation step of obtaining a correlation between the signal sequences of the detected vital sign detected from the imaged regions of the body and obtaining a correlation between the signal sequence of the sensed vital sign obtained during the sensor input step and at least one of the signal sequences of the detected vital sign detected from the imaged regions of the body;

an identity determination step of determining, based on the correlation between the signal sequences of the detected vital sign detected from the imaged regions of the body, that the imaged regions of the body belong to a same user and determining, based on the correlation between the signal sequence of the sensed vital sign obtained during the sensor input step and at least one of the signal sequences of the detected vital sign detected from the imaged regions of the body, that the imaged regions of the body belong to at least one of the operator of the controller and the wearer of the sensor; and an individual information management step of feeding back to a progression of the game at least one characteristic of the user, the characteristic being based on the detected signal sequence.

8. The individual discrimination method of claim 7, wherein:

the memory stores a plurality of images, each image being obtained by imaging one or more user body regions;

the vital sign detection step includes dividing each imaged region into a plurality of small regions, each of the small regions presenting a respective signal sequence, of a vital sign that cyclically varies, and includes detecting the respective signal sequences of each of the small regions;

the correlation obtained in the correlation calculation step is a correlation between the signal sequences detected from the small regions; and the identity determination step includes determining that certain imaged regions belong to the same user based on the correlation.

9. A non-transitory computer-readable medium encoded with a data structure for causing a computer to carry out:

a vital sign signal detection step of detecting a signal sequence of a detected vital sign that cyclically varies from a plurality of imaged regions of a body of a user playing a video game by using and referring to captured images of a predetermined number of frames from a memory that stores an image obtained by imaging a region of at least part of the body of the user;

a sensor input step of receiving input of a signal sequence of a sensed vital sign that cyclically varies from at least one of a sensor mounted in a controller operated by the user and a wearable sensor worn by the user;

a correlation calculation step of obtaining a correlation between the signal sequences of the detected vital sign detected from the imaged regions of the body and obtaining a correlation between the signal sequence of the sensed vital sign obtained during the sensor input step and at least one of the signal sequences of the detected vital sign detected from the imaged regions of the body;

an identity determination step of determining, based on the correlation between the signal sequences of the detected vital sign detected from the imaged regions of the body, that the imaged regions of the body belong to a same user and determining, based on the correlation between the signal sequence of the sensed vital sign obtained during the sensor input step and at least one of the signal sequences of the detected vital sign detected from the imaged regions of the body, that the imaged regions of the body belong to at least one of the operator of the controller and the wearer of the sensor; and an individual information management step of feeding back to a progression of the game at least one characteristic of the user, the characteristic being based on the detected signal sequence.

10. The non-transitory computer-readable medium of claim 9, wherein:

the memory stores a plurality of images, each image being obtained by imaging one or more user body regions;

the vital sign detection step includes dividing each imaged region into a plurality of small regions, each of the small regions presenting a respective signal sequence, of a vital sign that cyclically varies, and includes detecting the respective signal sequences of each of the small regions;

the correlation obtained in the correlation calculation step is a correlation between the signal sequences detected from the small regions; and the identity determination step includes determining that certain imaged regions belong to the same user based on the correlation.

* * * * *